US008353291B2

(12) United States Patent
Nicolazzi et al.

(10) Patent No.: US 8,353,291 B2
(45) Date of Patent: Jan. 15, 2013

(54) SYSTEMS AND METHODS FOR COMPENSATING FOR PRESSURE DROP IN A BREATHING ASSISTANCE SYSTEM

(75) Inventors: Pascal Nicolazzi, Gondreville (FR); Julien Gentner, Saunay (FR); Laurent Mougel, Sainte Marguerite (FR); Veronique Grillier-Lanoir, Besancon (FR); Hossein Nadjafizadeh, Villers-les-Nancy (FR)

(73) Assignee: Covidien LP, Mansfield, MA (US)

(*) Notice: Subject to any disclaimer, the term of this patent is extended or adjusted under 35 U.S.C. 154(b) by 921 days.

(21) Appl. No.: 12/410,310

(22) Filed: Mar. 24, 2009

(65) Prior Publication Data
US 2009/0241952 A1    Oct. 1, 2009

(30) Foreign Application Priority Data
Mar. 31, 2008  (EP) .................... 08006240

(51) Int. Cl.
*A61M 5/24*    (2006.01)
(52) U.S. Cl. ........ 128/204.21; 128/200.24; 128/204.23
(58) Field of Classification Search ........... 604/204.21, 604/200.24, 204.23
See application file for complete search history.

(56) References Cited

U.S. PATENT DOCUMENTS

| | | | |
|---|---|---|---|
| 4,967,744 A | 11/1990 | Chua | 128/204.18 |
| 5,099,836 A | 3/1992 | Rowland et al. | 128/204.23 |
| 5,111,827 A | 5/1992 | Rantala | 128/719 |
| 5,370,122 A | 12/1994 | Kunig et al. | 128/670 |
| 5,494,051 A | 2/1996 | Schneider, Sr. | 128/870 |
| 5,551,419 A * | 9/1996 | Froehlich et al. | 128/204.23 |
| 5,749,374 A | 5/1998 | Schneider, Sr. | 128/870 |
| 5,794,614 A | 8/1998 | Gruenke et al. | 128/204.21 |
| 5,969,429 A | 10/1999 | Rudolph et al. | 290/54 |
| 6,135,106 A | 10/2000 | Dirks et al. | |
| 7,089,930 B2 | 8/2006 | Adams et al. | 128/201.27 |
| 7,101,341 B2 | 9/2006 | Tsukashima et al. | 600/532 |
| 7,297,120 B2 | 11/2007 | Tsukashima et al. | 600/532 |

(Continued)

FOREIGN PATENT DOCUMENTS
FR    2824907 A    11/2002
(Continued)

OTHER PUBLICATIONS

International PCT Search Report and Written Opinion, PCT/US2009/055288, 17 pages, Mailed Dec. 4, 2009.
(Continued)

*Primary Examiner* — Lynne Anderson
*Assistant Examiner* — Bradley Philips (57) ABSTRACT

A breathing assistance system configured to determine pressure drop may include a gas delivery system configured to deliver gas toward a patient, one or more sensors configured to measure one or more parameters of gas delivered by the gas delivery system, a calibration module, and a pressure drop calculation module. The calibration module may be configured to perform one or more pressure drop calibration tests, each pressure drop calibration test measuring a pressure drop in gas flowing through a breathing assistance system apparatus at a particular flow rate; and based at least on the results of the one or more pressure drop calibration tests, generating a non-linear equation relating (a) pressure drop in gas flowing through the breathing assistance system apparatus with (b) flow rate of gas flowing through the breathing assistance system apparatus. The pressure drop calculation module may be configured to determine pressure drops in gas flowing through the breathing assistance system apparatus for various flow rates based at least on the non-linear equation.

11 Claims, 4 Drawing Sheets

U.S. PATENT DOCUMENTS

| | | | |
|---|---|---|---|
| 7,658,891 B1 | 2/2010 | Barnes | 422/186.03 |
| 7,985,254 B2 | 7/2011 | Tolkowsky | 128/203.14 |
| 2002/0116994 A1 | 8/2002 | Heinonen | |
| 2004/0015058 A1 | 1/2004 | Besson et al. | 600/301 |
| 2004/0118403 A1* | 6/2004 | O'Connor et al. | 128/204.23 |
| 2005/0217275 A1 | 10/2005 | Hendrickson et al. | 60/775 |
| 2006/0162728 A1* | 7/2006 | Delache et al. | 128/204.22 |
| 2007/0100222 A1 | 5/2007 | Mastrototaro et al. | 600/365 |
| 2008/0021339 A1 | 1/2008 | Gabriel et al. | 600/532 |
| 2008/0092898 A1 | 4/2008 | Schneider et al. | 128/206.28 |
| 2008/0167614 A1 | 7/2008 | Tolkowsky et al. | 604/131 |
| 2008/0177404 A1 | 7/2008 | Bonnat | 700/90 |
| 2008/0200776 A1 | 8/2008 | Schermeier et al. | 600/301 |
| 2009/0044805 A1 | 2/2009 | Somaiya et al. | |
| 2009/0320842 A1 | 12/2009 | Doherty et al. | 128/204.21 |
| 2011/0162647 A1 | 7/2011 | Huby et al. | 128/203.14 |
| 2012/0053431 A1* | 3/2012 | Mannheimer et al. | 600/323 |

FOREIGN PATENT DOCUMENTS

| | | | |
|---|---|---|---|
| FR | 2829942 A1 | 3/2003 | |
| WO | 90/04425 | 5/1990 | |
| WO | 2006/138578 A2 | 12/2006 | |

OTHER PUBLICATIONS

Application for Letters Patent, "System and Process for Supplying Respiratory Gas Under Pressure or Volumetrically," Inventor Claude Andreiux, 21 pages, Filed Jul. 27, 2004.

"GoodKnight® 425 GoodKnight® 425ST Clinician and Home Care Provider Manual", Puritan Bennett, Revision G, p. 25, referring to breathing circuits having an "internal pressure sensor line", Mar. 2010.

"Puritan Bennett CPAP / BiLEVEL Tubing with Internal Pressure Sensor Line", Printout of page from website www.cpapxchange.com, 2 pages, Printed Jun. 9, 2010.

International PCT Search Report and Written Opinion, PCT/US2010/035453, 13 pages, Sep. 20, 2010.

\* cited by examiner

| INDEX | A COEFF | B COEFF |
|---|---|---|
| 1 | 0.00183108 | 0 |
| 2 | 0.00549325 | -4.5777E-05 |
| 3 | 0.00640879 | -7.6295E-05 |
| 4 | 0.00823987 | -0.00016785 |
| 5 | 0.00915541 | -0.00022889 |
| 6 | 0.0109865 | -0.00038148 |
| 7 | 0.01281758 | -0.00056458 |
| 8 | 0.01373312 | -0.0006714 |
| 9 | 0.0155642 | -0.00091554 |
| 10 | 0.01739528 | -0.0011902 |
| 11 | 0.01922637 | -0.00149538 |
| 12 | 0.01922637 | -0.00149538 |
| 13 | 0.02197299 | -0.00204471 |
| 14 | 0.02380407 | -0.00244144 |
| 15 | 0.02471962 | -0.00265507 |
| 16 | 0.0265507 | -0.00311284 |
| 17 | 0.02838178 | -0.00360113 |
| 18 | 0.02838178 | -0.00360113 |
| 19 | 0.03205921 | -0.00471504 |
| 20 | 0.03205921 | -0.00471504 |
| 21 | 0.03480583 | -0.00563058 |
| 22 | 0.03572137 | -0.00595102 |
| 23 | 0.03755245 | -0.00662242 |
| 24 | 0.03755245 | -0.00662242 |
| 25 | 0.04029908 | -0.00772107 |
| 26 | 0.04213016 | -0.00848402 |
| 27 | 0.04396124 | -0.00927749 |
| 28 | 0.04487678 | -0.00968948 |
| 29 | 0.04670787 | -0.01054398 |
| 30 | 0.04670787 | -0.01054398 |
| 31 | 0.04945449 | -0.0119173 |
| 32 | 0.05128557 | -0.01286336 |
| 33 | 0.05311666 | -0.01383993 |
| 34 | 0.0540322 | -0.01434348 |
| 35 | 0.05586328 | -0.01538109 |
| 36 | 0.05677882 | -0.01591516 |
| 37 | 0.0586099 | -0.01701381 |
| 38 | 0.06044099 | -0.01814298 |
| 39 | 0.06135653 | -0.01872282 |
| 40 | 0.06410315 | -0.02049287 |
| 41 | 0.06501869 | -0.02110323 |
| 42 | 0.06501869 | -0.02110323 |
| 43 | 0.06868086 | -0.02366674 |
| 44 | 0.0695964 | -0.02432288 |
| 45 | 0.07142748 | -0.02566567 |
| 46 | 0.07234302 | -0.02635233 |
| 47 | 0.07417411 | -0.02775616 |
| 48 | 0.07508965 | -0.02847333 |
| 49 | 0.07692073 | -0.0299382 |
| 50 | 0.07875181 | -0.03143359 |
| 51 | 0.08058289 | -0.03295949 |
| 52 | 0.08241398 | -0.03451591 |
| 53 | 0.08332952 | -0.03530938 |
| 54 | 0.08424506 | -0.0361181 |
| 55 | 0.08607614 | -0.03776608 |
| 56 | 0.08790723 | -0.03944457 |
| 57 | 0.08973831 | -0.04115358 |
| 58 | 0.09156939 | -0.04289311 |
| 59 | 0.09248493 | -0.04377813 |
| 60 | 0.09340047 | -0.04467842 |
| 61 | 0.09616236 | -0.0474403 |
| 62 | 0.0970779 | -0.0483711 |
| 63 | 0.09890898 | -0.05026322 |
| 64 | 0.09982452 | -0.05122454 |
| 65 | 0.10257115 | -0.05415427 |
| 66 | 0.10257115 | -0.05415427 |
| 67 | 0.10440223 | -0.05616846 |
| 68 | 0.10714885 | -0.05923552 |
| 69 | 0.10806439 | -0.06027314 |
| 70 | 0.10897993 | -0.06132601 |
| 71 | 0.11172656 | -0.0645304 |
| 72 | 0.11172656 | -0.0645304 |
| 73 | 0.11447318 | -0.06782635 |
| 74 | 0.11538872 | -0.06894026 |
| 75 | 0.11721981 | -0.0711986 |
| 76 | 0.11905089 | -0.07348745 |
| 77 | 0.11996643 | -0.07464714 |
| 78 | 0.12088197 | -0.07582208 |
| 79 | 0.1236286 | -0.07939269 |
| 80 | 0.12545968 | -0.08178836 |

FIG. 4

SYSTEMS AND METHODS FOR COMPENSATING FOR PRESSURE DROP IN A BREATHING ASSISTANCE SYSTEM

RELATED PATENT APPLICATION

This application claims priority from European Patent Application No. 08006240.9 which was filed on Mar. 31, 2008, and is incorporated herein by reference in its entirety.

TECHNICAL FIELD

The present disclosure is related to breathing assistance systems, e.g., systems and methods for compensating for pressure drop in a breathing assistance system.

BACKGROUND

Breathing assistance systems such as ventilators and CPAP devices are used to provide various types of breathing assistance to patients. Typically, a patient is connected to a breathing assistance system by a connection system, which may include, for example, a patient circuit, a mask, nasal pillows, tracheal tube, and/or other conduits and connection devices. In some breathing assistance systems, the pressure delivered to the patient, or the pressure at the patient end of the connection system, is useful to the breathing assistance system, e.g., as feedback to the breathing assistance system or as an input for controlling the operation of the breathing assistance system.

When delivering gas to a patient via a patient connection system, it is often difficult or unfeasible to measure the pressure near the patient end of the connection system. Thus, pressure may be measured near the gas delivery device of the breathing assistance system (e.g., the ventilator outlet or CPAP box). In some instances, the pressure sensor is located within the ventilator or CPAP box housing. However, as known in the field, the pressure measured near the gas delivery device (i.e., near the end of the connection system opposite the patient) may not provide the most accurate data regarding the pressure at the patient end of the connection system, based at least in part on pressure drop effects in the patient connection system.

SUMMARY

According to one embodiment of the present disclosure, a breathing assistance system configured to determine pressure drop may include a gas delivery system configured to deliver gas toward a patient, one or more sensors configured to measure one or more parameters of gas delivered by the gas delivery system, a calibration module, and a pressure drop calculation module. The calibration module may be configured to perform one or more pressure drop calibration tests, each pressure drop calibration test measuring a pressure drop in gas flowing through a breathing assistance system apparatus at a particular flow rate; and based at least on the results of the one or more pressure drop calibration tests, generating a non-linear equation relating (a) pressure drop in gas flowing through the breathing assistance system apparatus with (b) flow rate of gas flowing through the breathing assistance system apparatus. The pressure drop calculation module may be configured to determine pressure drops in gas flowing through the breathing assistance system apparatus for various flow rates based at least on the non-linear equation.

According to another embodiment of the present disclosure, a method for determining pressure drop in an apparatus of a breathing assistance system is provided. One or more pressure drop calibration tests are performed, each pressure drop calibration test measuring a pressure drop in gas flowing through a breathing assistance system apparatus at a particular flow rate. A non-linear equation is generated based at least on the results of the one or more pressure drop calibration tests, the non-linear equation relating (a) pressure drop in gas flowing through the breathing assistance system apparatus with (b) flow rate of gas flowing through the breathing assistance system apparatus. Pressure drops in gas flowing through the breathing assistance system apparatus may then be determined for various flow rates based at least on the generated non-linear equation.

According to another embodiment of the present disclosure, a system for determining pressure drop in an apparatus of a breathing assistance system includes a calibration module and a pressure drop calculation module. The calibration module may be configured to perform one or more pressure drop calibration tests, each pressure drop calibration test measuring a pressure drop in gas flowing through a breathing assistance system apparatus at a particular flow rate; and based at least on the results of the one or more pressure drop calibration tests, generate a non-linear equation relating (a) pressure drop in gas flowing through the breathing assistance system apparatus with (b) flow rate of gas flowing through the breathing assistance system apparatus. The pressure drop calculation module may be configured to determine pressure drops in gas flowing through the breathing assistance system apparatus for various flow rates based at least on the non-linear equation.

According to another embodiment of the present disclosure, a method for facilitating the determination of a pressure drop in an apparatus of a breathing assistance system is provided. Multiple pressure drop calibration tests are preformed, each pressure drop calibration test measuring a pressure drop in gas flowing through a breathing assistance system apparatus at a particular flow rate. Coefficients for multiple linear line segments are calculated based on the results of the multiple pressure drop calibration tests, the multiple linear line segments collectively approximating a non-linear relationship between (a) pressure drop in gas flowing through the breathing assistance system apparatus and (b) flow rate of gas flowing through the breathing assistance system apparatus. The calculated coefficients for the multiple linear line segments are stored such that the calculated coefficients may be accessed while providing breathing assistance to a patient to determine pressure drops in gas flowing through the breathing assistance system apparatus for various flow rates.

According to another embodiment of the present disclosure, a method for determining pressure drop in an apparatus of a breathing assistance system is provided. A look-up table of coefficients for linear equations representing multiple line segments is stored, the line segments collectively approximating a non-linear relationship between (a) pressure drop in gas flowing through the breathing assistance system apparatus and (b) flow rate of gas flowing through the breathing assistance system apparatus. A measured flow rate value for gas flowing through the breathing assistance system apparatus is received, and one or more coefficients corresponding to a particular line segment corresponding with the measured flow rate value is accessed from the stored look-up table. The one or more accessed coefficients corresponding to the particular line segment may then be used to calculate a pressure drop corresponding with the measured flow rate value.

BRIEF DESCRIPTION OF THE DRAWINGS

Some embodiments of the disclosure may be understood by referring, in part, to the following description and the accompanying drawings, in which like reference numbers refer to the same or like parts and wherein:

FIG. 3 illustrates an example look-up table of coefficient pairs for line segment equations for use in calculating pressure drops for various flow rate values, according to an example embodiment of the disclosure.

DETAILED DESCRIPTION

Selected embodiments of the disclosure may be understood by reference, in part, to FIGS. 1-4, wherein like numbers refer to same and like parts. The present disclosure relates generally to methods for compensating for pressure drop in a breathing assistance system. As known in the field, when delivering gas to a patient via a patient connection system (e.g., a patient circuit), the pressure measured near the outlet of the gas delivery system (e.g., ventilator or CPAP box) may not provide accurate data regarding the actual pressure delivered to the patient, based at least in part on pressure drop inherent in the patient circuit or other conduit. In particular, due to such inherent pressure drop, the pressure measured near the outlet of the gas delivery system is typically greater than the actual pressure delivered to the patient in the case of positive flow in the direction of the patient, and lower than the actual pressure delivered to the patient in the case of negative flow in the direction of the patient. However, it is often necessary or desirable to measure the pressure near the outlet of the gas delivery system instead of at the patient end of the patient connection system. Accordingly, the present disclosure provides systems and methods for accurately calculating, or estimating, the pressure drop in the patient connection system for different gas flow rates, such that the gas delivery system can properly compensate for the pressure drop.

Figure 1:
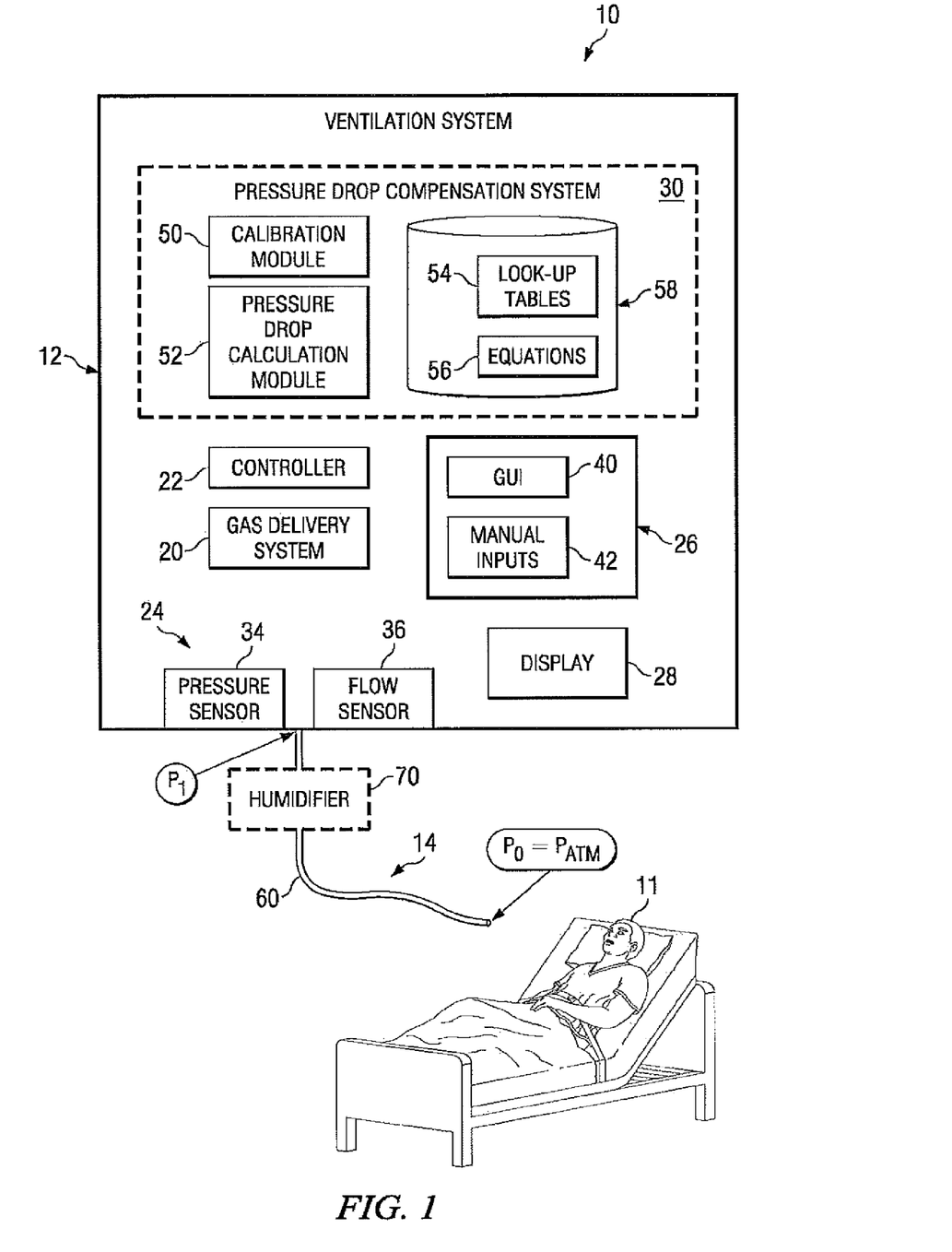
FIG. 1 illustrates an example breathing assistance system 10 for communicating gas to and/or from a patient, and for calculating and compensating for pressure drop associated with such gas communication, according to one embodiment of the disclosure.

FIG. 1 illustrates an example breathing assistance system 10 for communicating gas to and/or from a patient, and for calculating and compensating for pressure drop associated with such gas communication, according to one embodiment of the disclosure. Breathing assistance system 10 may be generally configured to provide breathing assistance (e.g., providing ventilation and/or treating an apnea or other breathing condition) to a patient 11. Breathing assistance system 10 may include a ventilation system 12 and a connection system 14 for connecting ventilation system 12 to patient 11.

Ventilation system 12 may comprise any device, apparatus, or system for delivering breathing gas to a patient, e.g., a ventilator, a respirator, a CPAP device, or a BiPAP device. Connection system 14 may be generally configured to deliver gas from ventilation system 12 to patient 11 and/or to communicate exhaust gas away from patient 11. For example, connection system 14 may comprise any suitable type of breathing circuit (e.g., a single-limb or dual-limb circuit) and/or a patient connection apparatus. For instance, connection system 14 may include a 6-foot patient circuit. A patient connection apparatus may include any device or devices configured to connect the breathing circuit to one or more breathing passageways of patient 11. For example, the patient connection apparatus may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth.

Ventilation system 12 may include a gas delivery system 20, a controller 22, one or more sensors 24, user interfaces 26, a display system 28, and a pressure drop compensation system 30.

Gas delivery system 20 may include any device or devices configured to generate, supply, and/or deliver gas (e.g., pressurized air) toward patient 11 via connection system 14. For example, gas delivery system 20 may comprise a device capable of generating pressurized air (e.g., a motorized blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas. In some embodiments, gas delivery system 20, in cooperation with other components of ventilation system 12 (e.g., an exhalation valve) may generate both positive and negative gas flows toward patient 11. For example, a positive gas flow may be generated as gas is delivered to patient 11 during inhalation, while a negative gas flow may be generated as exhaust gas is communicated from patient 11 during exhalation.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Controller 22 may be operable to control gas delivery system 20 to control the delivery of gas to and/or from patient 11 based on various input received from a user (e.g., via a touch screen and/or other user interfaces provided by ventilation system 12), data received from pressure drop compensation system 30, and/or data received from one or more sensors 24. For example, controller 22 may regulate the pressure and/or flow rate of gas delivered to and/or from a patient based at least on pressure and/or flow data received from sensors 24 and pressure drop data received from pressure drop compensation system 30.

Controller 22 may include, or have access to, one or more processors, memory devices, and any other suitable hardware or software. The one or more memory devices may store instructions (e.g., any suitable software, algorithms, or other logic or instructions that may be executed by one or more processors) for automatically controlling the operation of ventilation system 12 (e.g., controlling the pressure and/or flow rate output by gas delivery system 20) based on any of the various input data discussed herein.

Any one or more sensors 24 may be provided for sensing, detecting, and/or monitoring one or more parameters related to the ventilation of patient 11, e.g., parameters regarding the ventilation provided by ventilation system 12 and/or physiological parameters regarding patient 11. For example, sensors 24 may include one or more devices for measuring various parameters of gas flowing to or from patient 11 or ventilation system 12, e.g., the pressure, flow rate, flow volume, temperature, gas content, and/or humidity of such gas flow.

In certain embodiments, sensors 24 may include a pressure sensor 34 and a flow sensor 36 for measuring the pressure and flow, respectively, of gas delivered from gas delivery system 20. Sensors 34 and 36 may be located at any suitable location in system 10. For example, each sensor 24 may be integrated with or coupled to ventilation system 12, integrated with or coupled to connection system 14, coupled to patient 11, or otherwise associated with system 10.

In certain embodiments, pressure sensor 34 is located at or proximate a gas outlet of ventilation system 12 (e.g., at or proximate an outlet of gas delivery system 20). For example, pressure sensor 34 may be located inside or just outside a housing or enclosure of ventilation system 12. Thus, pressure sensor 34 may be positioned to measure the pressure of gas flow exiting ventilation system 12 or gas delivery system 20, or the pressure of gas flow entering connection system 14, as generally indicated by arrow "P1" in FIG. 1.

In addition, in some embodiments, flow sensor 36 may be located at or proximate a gas outlet of ventilation system 12 (e.g., at or proximate an outlet of gas delivery system 20). For example, flow sensor 36 may be located inside or just outside a housing or enclosure of ventilation system 12. Thus, flow sensor 36 may be positioned to measure the flow rate of gas flow exiting ventilation system 12 or gas delivery system 20, or the flow rate of gas flow entering connection system 14.

In some embodiments or configurations, breathing assistance system 10 may include a humidifier 70, which may be integral with or separate from, ventilation system 12. The humidifier may be located and connected to system 10 in any suitable manner. Typically, the humidifier 70 is located between the gas delivery system of the ventilation system 12 and the patient In some embodiments, humidifier 70 is located downstream of pressure sensor 34, and may affect (e.g., increase) the pressure drop between pressure sensor 34 and the patient end of connection system 14. Humidifier 70 may include any known type of humidifier for use with a ventilator, CPAP system, or other type of breathing assistance system 10.

User interfaces 26 may include any suitable device or devices allowing a user to interface with breathing assistance system 10, e.g., to control ventilation system 12, to navigate through various display screens, to make selections, and/or to set, modify, or otherwise control various parameters regarding system 10. For example, user interfaces 26 may allow a user to input desired performance parameters (e.g., pressure or flow rate) that may be communicated to controller 22 to control the operation of gas delivery system 20 and/or other components of system 10.

User interfaces 26 may include a graphic user interface (GUI) 40, one or more manual input devices 42 separate from the GUI, and/or any other input devices. GUT 40 may include a touch screen configured to display various information and provide an interface for accepting input from user (e.g., to navigate through various screens, to make selections, to set or modify various parameters, to change or configure the display, etc.). Manual input devices 42 may include any physical buttons, knobs, dials, switches, levers) or any other devices that may be manipulated by a user.

Display device 28 may comprise a screen or any other device suitable for visually displaying medical data. For example, display device 28 may include a monitor, an LCD screen, LEDs, or any other visual device. In some embodiments, display device 28 and user interfaces 26 may be at least partially integrated, e.g., where ventilation system 12 includes a touch screen or other GUI 40.

Pressure drop compensation system 30 may be generally configured to calculate the pressure drop of gas flowing through an apparatus of system 10 (e.g., connection system 14 or a portion thereof) such that controller 22 may compensate for such pressure drop in controlling or regulating gas delivery system 20. Pressure drop compensation system 30 may include a calibration module 50, a pressure drop calculation module 52, and one or more look-up tables 54 and/or equations 56 stored in memory 58.

Calibration module 50 is generally configured to calibrate an apparatus 60 of system 10 for pressure drop calculations. Apparatus 60 may comprise any one or more components of system 10 in which gas may experience a pressure drop. For example, apparatus 60 may comprise connection system 14 or a portion thereof, e.g., a patient circuit or patient hose with or without an attached patient connection apparatus (e.g., as defined above), with or without an attached humidifier 70, or any combination of such components.

Calibration module 50 may be configured to perform one or more calibration tests for a particular type or a particular instance of an apparatus 60 in order to generate look-up tables 54 and/or equations 56 stored in memory 58. In some embodiments, calibration module 50 may calibrate apparatus 60 during a calibration mode performed before connecting patient 11 to connection system 14 and/or before providing breathing assistance to patient 11. In other embodiments, e.g., where calibration data is preloaded into memory 58, calibration module 50 may not be included.

Look-up tables 54 and/or equations 56 include data that may be used by pressure drop calculation module 52 for calculating a pressure drop in apparatus 60 while providing breathing assistance to patient 11. In some embodiments, look-up tables 54 and/or equations 56 may be preloaded into memory 58. In other embodiments, look-up tables 54 and/or equations 56 may be generated by calibration module 50, as discussed above.

Equations 56 may include:
one or more equations for calculating or estimating the pressure drop in gas flowing through apparatus 60 (e.g., due to resistance and variances associated with apparatus 60) as a function of the flow rate of gas flowing through apparatus 60; and/or
one or more equations for calculating or estimating the "mask pressure," compensating for the pressure drop of the gas flow through apparatus 60. As used herein, the term "mask pressure" refers to the pressure at the outlet or patient end of apparatus 60, regardless of whether a mask is used in the particular configuration.

Examples of such equations 56 include Equations (1) through (6b), discussed below.

Equations 56 may be used to calculate or estimate pressure drop for positive and/or negative flow rates through apparatus 60 (e.g., in some configurations, a negative flow rate may be experienced during exhalation). In some embodiments, the same equations 56 may be used for both positive and negative flow situations. In other embodiments, separate equations 56 may be used for positive and negative flow situations. For example, Equations (1) through (6b) provided below include separate equations 56 for positive and negative flow situations.

Look-up tables 54 may include, for example, coefficients for any of equations 56, For example, as discussed below, in some embodiments, a look-up table 54 may include coefficients defining each of multiple (e.g., 80) different linear line segments that collectively approximate a non-linear function between pressure drop and flow rate. Such coefficients in look-up tables 54 may be easily accessed and used for calculating or estimating the pressure drop or mask pressure while providing breathing assistance to a patient 11.

In some embodiments, look-up tables 54 may include different tables corresponding to different types and/or configurations of apparatuses 60. For example, look-up tables 54 may include a first table of equation coefficients for use with a 6' patient circuit and a second table of equation coefficients for use with an 8' patient circuit. As another example, look-up tables 54 may include a first table of equation coefficients for a configuration using a 6' patient circuit and including a humidifier 70, and a second table of equation coefficients for a configuration using the same 6' patient circuit, but not including a humidifier 70.

In addition, in embodiments in which the same equations 56 may be used for both positive and negative flow situations, look-up tables 54 may include one set of equation coefficients for positive flow situations and another set of equation coefficients for negative flow situations. In embodiments in which different equations 56 may be used for positive and negative flow situations (e.g., Equations (1) through (6b) provided below), the same set of equation coefficient may be used for both positive and negative flow situations.

Pressure drop calculation module 52 may be configured to use look-up tables 54 and/or equations 56 stored in memory 58, along with any other suitable data (e.g., data from sensors 24) for calculating a pressure drop in apparatus 60, e.g., while providing breathing assistance to patient 11. For example, in some embodiments, pressure drop calculation module 52 may use one or more equations 56 and/or equation coefficients store in a look-up table 54 to calculate pressure drop in apparatus 60 based on measured flow rate values received from flow sensor 36.

Calibration module 50 and/or pressure drop calculation module 52 may include, or have access to, one or more processors (e.g., a microprocessor, a microcontroller, DSP, ASIC, FPGA, or any other suitable processor), tangible memory devices (e.g., RAM, DRAM, ROM, EPROM, Flash memory, one or more hard disks, and/or any other memory or storage device), and any other suitable hardware, software, or firmware. The one or more memory devices may store instructions (e.g., any suitable software, algorithms, or other logic or instructions that may be executed by one or more processors) for providing any of the functionality of such modules discussed herein.

Example Method 1

Line Segment Calibration

In some embodiments, calibration module 50 may be configured to calibrate a particular type, configuration, or instance of apparatus 60 by performing multiple pressure drop calibration tests and determining equation coefficients for multiple straight line segments approximating a non-linear relationship between pressure drop through apparatus 60 and flow rate through apparatus 60. Each calibration test may include determining a pressure drop in gas flowing through apparatus 60 at a particular flow rate.

Each calibration test may include delivering air through apparatus 60 with the distal end of apparatus 60 (i.e., opposite the end connected to ventilation system 12) left open such that the pressure at the distal end is atmospheric pressure, as indicated in FIG. 1 as $P_0$. Using such technique, the pressure $P_1$ measured adjacent the outlet of ventilation system 12 may be recorded as the pressure drop through apparatus 60.

Calibration module 50 may perform calibration tests at any number of different flow rates, which may include positive flow rates, negative flow rates, or both. For example, calibration module 50 may perform calibration tests at 10 or more different flow rates to obtain 10 or more corresponding pressure drop values. In certain embodiments, calibration module 50 may perform about 80 calibration tests at 80 different flow rates to obtain 80 corresponding pressure drop values.

Figure 2:
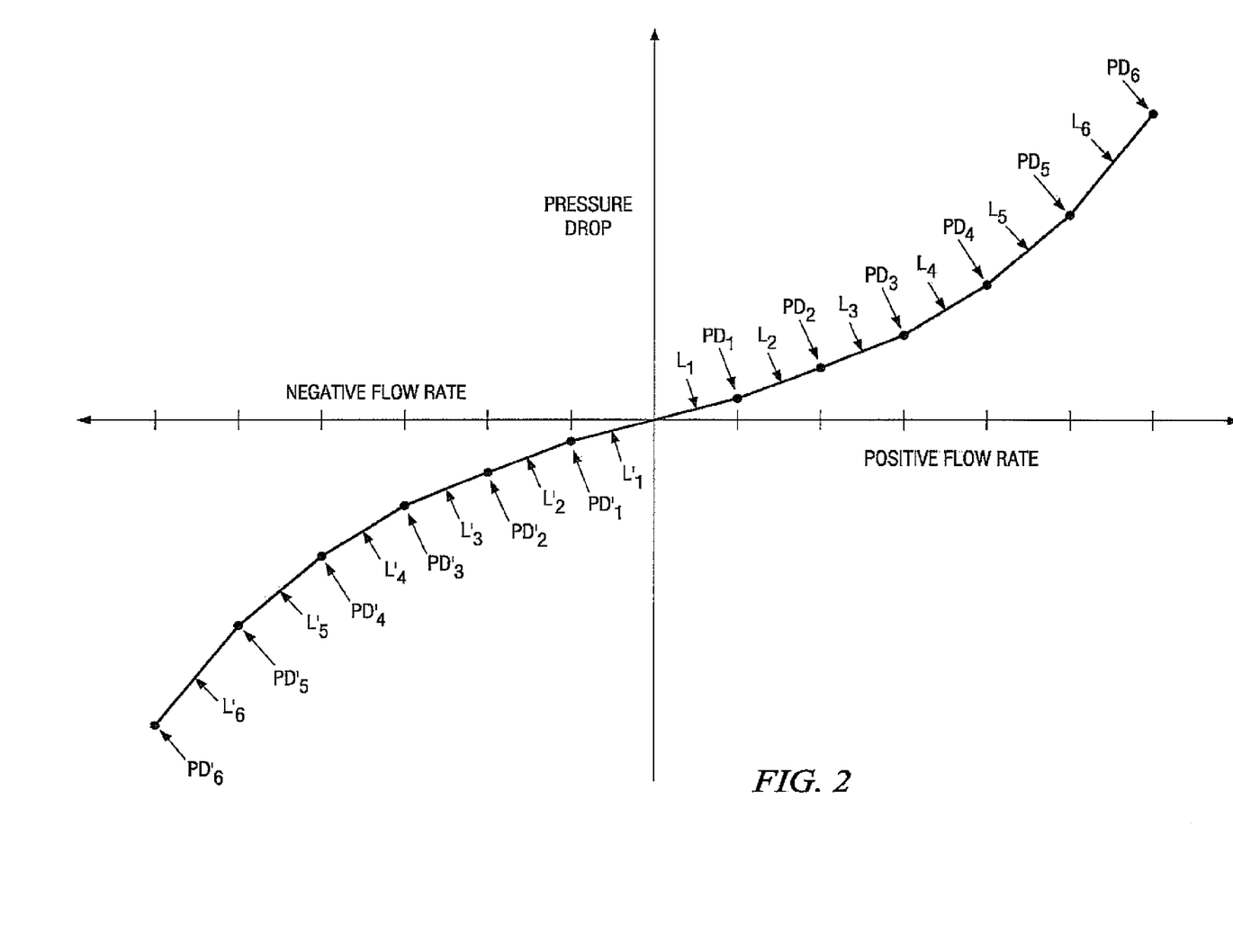
FIG. 2 illustrates an example graph of pressure drop versus flow rate of gas flow through an apparatus, including calibration test results and corresponding line segments, according to an example embodiment.

FIG. 2 illustrates an example plot of the results of calibration tests of an apparatus 60 at six positive flow rates (providing pressure drop data points $PD_1$ through $PD_6$) and six negative flow rates (providing pressure drop data points $PD_1'$ through $PD_6'$).

Although six positive and six negative data points are shown for illustrative purposes, any number (e.g., 80) of data points may be determined. In some embodiments, calibration tests may be performed and recorded using both positive and negative flow rates. In other embodiments, calibration tests may be performed and recorded using positive flow rates, and the results may simply be mirrored to provide the negative flow rate test results, which may reduce the total number of calibration tests by half.

As shown in FIG. 2, the pressure drop data points may indicate a non-linear relationship between pressure drop and flow rate.

After performing the various calibration tests at different flow rates to generate the pressure drop data points, calibration module 50 may determine equation coefficients for straight line equations corresponding to the pressure drop data points. For example, calibration module 50 may determine coefficients $A_i$ and $B_i$ for each straight line $L_1$ through $L_6$ connecting adjacent pressure drop data points, according to the linear equation:

$$\text{Pressure Drop} = A_i * ABS(\text{Flow}) + B_i \quad (1)$$

where "ABS(Flow)" is the absolute value of the measured flow rate (e.g., by flow sensor 36).

Thus, calibration module 50 may determine six pairs of coefficients $A_i$ and $B_i$, each coefficient pair corresponding to one of the six lines $L_1$ through $L_6$. These coefficient pairs may be stored in a look-up table 54 for use by pressure drop calculation module 52 to calculate estimated mask pressure values based on flow rate values measured by flow sensor 36 while providing breathing assistance to a patient 11. As discussed below, these coefficient pairs may be used to calculate estimated mask pressure values for both positive flow and negative flow situations.

For example, for positive flow situations (e.g., during inhalation), pressure drop calculation module 52 may calculate estimated mask pressure values using the equation:

$$\text{Estimated Mask Pressure} = \text{Measured } P_1 - \text{Pressure Drop} \quad (2a)$$

or, substituting Equation (1) into Equation (2a):

$$\text{Estimated Mask Pressure} = \text{Measured } P_1 - (A_i * (\text{Flow}) + B_i) \quad (3a)$$

where "Measured $P_1$" is the measured pressure at location $P_1$, and "Flow" is the measured flow rate (e.g., by flow sensor 36).

Similarly, for negative flow situations (e.g., during exhalation), pressure drop calculation module 52 may calculate estimated mask pressure values using the equation:

$$\text{Estimated Mask Pressure} = \text{Measured } P_1 + \text{Pressure Drop} \quad (2b)$$

or, substituting Equation (1) into Equation (2b):

$$\text{Estimated Mask Pressure} = \text{Measured } P_1 + (A_i * \text{ABS(Flow)} + B_i) \quad (3b)$$

where "Measured $P_1$" is the measured pressure at location $P_1$, and "ABS(Flow)" is the absolute value of the measured flow rate (e.g., by flow sensor 36).

As discussed above, multiple look-up tables 54 may be generated and/or maintained in memory 58, corresponding to any number of different types, configurations, or instances of apparatus 60. Pressure drop calculation module 52 may access the appropriate look-up tables 54 based on input received from a user (e.g., via a user selection of a particular configuration or type of patient circuit) or automatically via other components of ventilation system 12 and/or connection system 14 (e.g., ventilation system 12 may automatically identify the particular type of patient circuit connected to ventilation system 12, or whether a humidifier is connected to ventilation system 12, and send appropriate signals to pressure drop calculation module 52.

FIG. 3 illustrates an example look-up table 54 including 80 coefficient pairs for 80 line segments, for an example in which apparatus 60 comprises a 6 foot patient hose without a humidifier, according to an example embodiment of the disclosure. The coefficient pairs in look-up table 54 may be used for calculating pressure drops in both positive flow and negative flow situations. For example, the same coefficient pair may be used for a measured flow rate of 1.5 l/s and a measured flow rate of −1.5 l/s.

In some embodiments, calibration module 50 in ventilation system 12 may perform the calibration process discussed above for a particular apparatus 60 connected to ventilation system 12, and store the results in one or more look-up tables 54. Thus, ventilation system 12 may be used to calibrate a particular type, configuration, and/or instance of apparatus 60 to be used for providing breathing assistance to a patient 11. Such calibration may be performed at any suitable time prior to providing breathing assistance to a patient 11, e.g., just prior to initiating breathing assistance to patient 11, upon the initial configuration of ventilation system 12, or upon receiving a new type of apparatus 60 (e.g., a new brand or model of patient circuit).

In some embodiments, the calibration process discussed above may be performed on another ventilation system or during manufacturing of ventilation system 12, and look-up tables 54 may be pre-loaded into memory 58 in ventilation system 12. In still other embodiments, one or more look-up tables 54 may be pre-loaded into memory 58, but calibration module 50 may subsequently be used to generate and store additional look-up tables 54 (e.g., for new types or configurations of apparatus 60).

In alternative embodiments, calibration module 50 may calculate or determine a non-linear function between pressure drop through apparatus 60 and flow rate through apparatus 60. For example, calibration module 50 may generate one or more non-linear equation(s) that approximates the relationship between pressure drop and flow rate using some or all of the calibration test data points. Such non-linear equation(s) may include equations of any order (e.g., second order, third order, fourth order, etc.), which order may be selected by a user or selected automatically by calibration module 50. Calibration module 50 may generate such non-linear equation(s) using any known curve-fitting techniques or other suitable techniques.

Example Method 2

Automatic Calibration

In some embodiments, calibration module 50 may be configured to automatically calibrate a particular type, configuration, or instance of apparatus 60 by generating a non-linear function between pressure drop through apparatus 60 and flow rate through apparatus 60, and determining equation coefficients for multiple straight line segments approximating the generated non-linear function. The pressure drop in gas flowing through apparatus 60 (e.g., due to resistance and variances associated with apparatus 60) as a function of the flow rate of gas flowing through apparatus 60. may be written as:

$$\text{Pressure Drop} = \text{Function (Flow)} \quad (4)$$

where:
"Pressure Drop" is the pressure drop in gas flowing through apparatus 60, and
"Flow" is the flow rate of gas flowing through apparatus 60.

Figure 4:
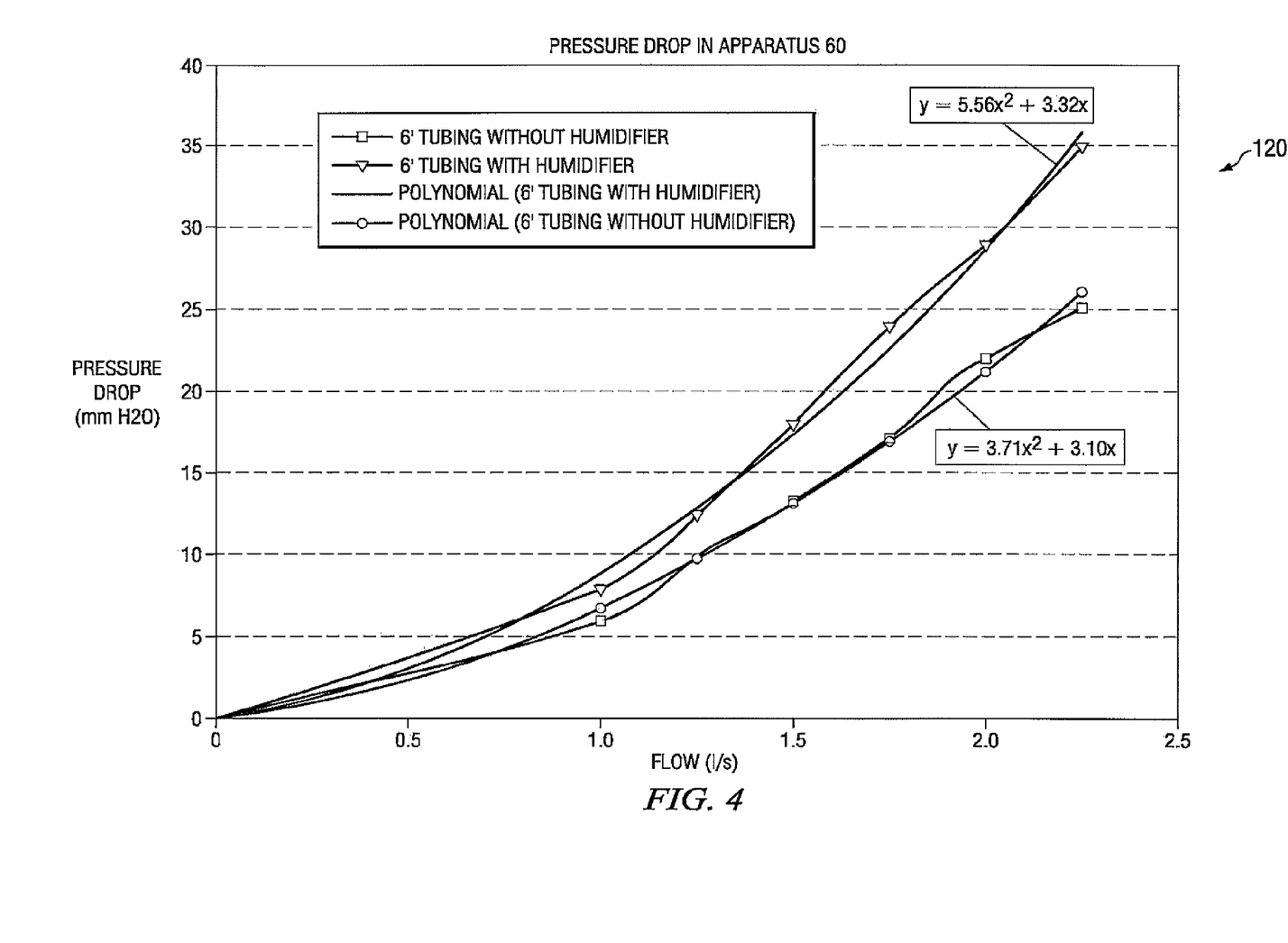
FIG. 4 is a graph illustrating example empirical results obtained from testing various configurations of connection system apparatuses, which illustrates the non-linear nature of the relationship between pressure drop and flow rate through such connection system apparatuses.

FIG. 4 is a graph 120 illustrating example empirical results obtained from testing two configurations of apparatus 60—a 6' patient circuit without a humidifier and the 6' patient circuit with an attached humidifier—which illustrates the non-linear nature of the relationship between pressure drop and flow rate. Although graph 120 only shows results for positive flow rates, similar results (but mirrored across the x- and y-axes) may be obtained for negative flow rates.

As shown in FIG. 4, based on these and other empirical results, it has been observed that the pressure drop as a function of flow rate can be estimated as a second degree polynomial equation, which may be written as follows:

$$\text{Pressure Drop} = X * (\text{Flow})^2 + Y * \text{ABS(Flow)} \quad (5)$$

where:
"Pressure Drop" is the pressure drop in gas flowing through apparatus 60,
"ABS(Flow)" is the absolute value of the flow rate through apparatus 60, and
"X" and "Y" are coefficients.

Calibration module 50 may solve for coefficients X and Y in Equation (5) by performing one or more pressure drop calibration tests at one or more positive and/or negative flow rates. Such calibration tests may be performed as discussed above, e.g., by delivering air through apparatus 60 with the distal end of apparatus 60 (i.e., opposite the end connected to ventilation system 12) left open such that the pressure at the distal end is atmospheric pressure, as indicated in FIG. 1 as $P_0$.

Equation (5), including coefficients X and Y solved based on the calibration test(s), may be stored in memory 58. With coefficients X and Y being solved, Equation (5) may be used either directly or indirectly for calculating mask pressure values based on positive and/or negative flow rate values measured by flow sensor 36 while providing breathing assistance to a patient 11, as discussed below.

Direct use of Equation (5). In some embodiments, pressure drop calculation module 52 may use Equation (5) (including solved coefficients X and Y) directly for calculating estimated mask pressure values. Flow sensor 36 may measure and communicate flow rate values while providing breathing assistance to a patient 11. Pressure drop calculation module 52 may plug the flow rate values directly into Equation (5) to calculate estimated pressure drop values.

Further, for positive flow situations (e.g., during inhalation), Equation (5) may be substituted into Equation (3a) to obtain Equation (6a):

$$\text{Estimated Mask Pressure} = \text{Measured } P_1 - [X^*(\text{Flow})^2 + Y^*(\text{Flow})] \quad (6a)$$

where "Measured $P_1$" is the measured pressure at location $P_1$, and "Flow" is the measured flow rate (e.g., by flow sensor 36), Thus, pressure drop calculation module 52 may plug received flow rate values directly into Equation (6a) to directly calculate estimated mask pressure values in positive flow situations.

Similarly, for negative flow situations (e.g., during exhalation), Equation (5) may be substituted into Equation (3b) to obtain Equation (6b):

$$\text{Estimated Mask Pressure} = \text{Measured } P_1 + [X^*(\text{Flow})^2 + Y^*ABS(\text{Flow})] \quad (6b)$$

where "Measured $P_1$" is the measured pressure at location $P_1$, "Flow" is the measured flow rate (e.g., by flow sensor 36), and "ABS(Flow)" is the absolute value of "Flow"

Thus, pressure drop calculation module 52 may plug received flow rate values directly into Equation (6b) to directly calculate estimated mask pressure values in negative flow situations.

Indirect use of Equation (5). In some embodiments, Equation (5) (including solved coefficients X and Y) may be used indirectly for calculating estimated mask pressure values. In such embodiments, calibration module 50 may approximate the non-linear relationship between pressure drop and flow rate defined by Equation (5) using a number (e.g., 80) straight line segments. Calibration module 50 may calculate coefficients for equations representing each of such straight line segments, and store such coefficients in a look-up table 54.

For example, calibration module 50 may calculate coefficient pairs $A_i$ and $B_i$ for Equations (3a) and (3b) corresponding to each line segment.

$$\text{Estimated Mask Pressure} = \text{Measured } P_1 - (A_i^*\text{Flow} + B_i) \quad (3a)$$

$$\text{Estimated Mask Pressure} = \text{Measured } P_1 + (A_i^*ABS(\text{Flow}) + B_i) \quad (3b)$$

Calibration module 50 may use any known or suitable techniques for calculating the coefficient pairs $A_i$ and $B_i$ for the line segments approximating the non-linear curve defined by Equation (5). For example, calibration module 50 may determine the slope of the curve defined by Equation (5) at each of a number (e.g., 80) of flow rate values, record the corresponding slopes as $A_i$ for each respective flow rate value (or for the data intervals corresponding to each respective flow rate value), and calculate the corresponding $B_i$ values. As another example, calibration module 50 may calculate the pressure drop values for each of a number (e.g., 80) of flow rate values according to Equation (5), and use each adjacent pair of calculated pressure drop values as end-points for the multiple (e.g., 80) line segments collectively approximating the curve of Equation (5).

Regardless of the technique used for calculating the coefficient pairs $A_i$ and $B_i$ for the multiple line segments approximating the non-linear curve of Equation (5), such calculated coefficient pairs $A_i$ and $B_i$ may be stored in a look-up table 54. Later, while providing breathing assistance to patient 11, pressure drop calculation module 52 may access such look-up table 54 to calculate estimated mask pressure values based on flow rate values measured by flow sensor 36 using Equation (3a) (for positive flow rates) or Equation (3b) (for negative flow rates).

Patient Selectable Menu for Using Pre-Set Vs. Auto Calibration

Ventilation system 12 may initiate any of the calibration processes discussed above in various manners. In some embodiments, ventilation system 12 may allow the user to initiate a calibration of an apparatus 60 connected to ventilation system 12. For example, ventilation system 12 may include one or more user interfaces 26 (e.g., GUI 40 or one or more manual input devices 42) allowing the user to (a) initiate an automatic calibration of apparatus 60, (b) initiate a line segment calibration of apparatus 60, (e) instruct the ventilation system 12 to access stored look-up tables 54 and/or equations 56 for a particular apparatus 60, and/or (d) enter data identifying apparatus 60 (e.g., the type of patient circuit and/or whether a humidifier is attached). For example, ventilation system 12 may include an "auto calibration" button and a "line segment calibration" button for initiating such calibration processes. As another example, a user interface 26 may allow the user to select various parameters for a calibration process, e.g., a number of calibration tests to be performed, a range of flow rates for the calibration tests, a number of line segments to be calculated, and/or an order of a non-linear equation (e.g., third order equation) to be calculated (e.g., by curve fitting) to approximate the calibration test data. In some embodiments, GUI 40 may include any suitable buttons and/or menus for selecting and/or inputting any of the parameters discussed above.

In some embodiments, ventilation system 12 may be configured to automatically access the appropriate look-up tables 54 and/or equations 56 based on data entered by the user identifying apparatus 60 (e.g., a serial number, part number, or type of patient circuit and/or whether a humidifier is attached). In other embodiments, ventilation system 12 may be configured to automatically obtain identification information regarding apparatus 60, and access the corresponding look-up tables 54 and/or equations 56. For example, ventilation system 12 may be configured to automatically read data stored in non-volatile memory embedded in a patient circuit when the patient circuit is connected to ventilation system 12. In such embodiments, ventilation system 12 may calibrate an apparatus 60, or access the appropriate look-up tables 54 and/or equations 56, automatically without user input.

It will be appreciated that while the disclosure is particularly described in the context of measuring and/or compensating for pressure drop in a conduit of a breathing assistance system, the apparatuses, techniques, and methods disclosed herein may be similarly applied in other contexts, e.g., measuring and/or compensating for pressure drops in gas flow in other medical devices. Additionally, it should be understood that various changes, substitutions and alterations can be made herein without departing from the spirit and scope of the disclosure as illustrated by the following claims.

What is claimed is:

1. A breathing assistance system configured to determine pressure drop, comprising:
   a gas delivery system configured to deliver gas toward a patient;
   one or more sensors configured to measure one or more parameters of gas delivered by the gas delivery system;
   a calibration module configured to:

perform one or more positive-pressure pressure drop calibration tests, each positive-pressure pressure drop calibration test measuring a pressure drop in gas flowing through a breathing assistance system apparatus at a particular positive flow rate; and perform one or more negative-pressure pressure drop calibration tests, each negative-pressure pressure drop calibration test measuring a pressure drop in gas flowing through a breathing assistance system apparatus at a particular negative flow rate; and based at least on the results of the one or more pressure drop calibration tests, generate:

(a) a positive-pressure non-linear equation relating (a) pressure drop in gas flowing through the breathing assistance system apparatus with (b) flow rate of gas flowing through the breathing assistance system apparatus, for positive-pressure gas flow; and (b) a negative-pressure non-linear equation relating (a) pressure drop in gas flowing through the breathing assistance system apparatus with (b) flow rate of gas flowing through the breathing assistance system apparatus, for negative-pressure gas flow;

wherein the negative-pressure non-linear equation is different than the positive-pressure non-linear equation; and a pressure drop calculation module configured to determine pressure drops in gas flowing through the breathing assistance system apparatus for various flow rates based at least on the non-linear equation.

2. A breathing assistance system according to claim 1, wherein:

generating a positive-pressure non-linear equation relating pressure drop with flow rate for positive-pressure gas flow comprises calculating one or more first coefficients for a non-linear equation relating pressure drop with flow rate; and generating a negative-pressure non-linear equation relating pressure drop with flow rate for positive-pressure gas flow comprises calculating one or more second coefficients for a non-linear equation relating pressure drop with flow rate.

3. A breathing assistance system according to claim 2, wherein the one or more first coefficients for the positive-pressure non-linear equation are different than the one or more second coefficients for the negative-pressure non-linear equation.

4. A breathing assistance system according to claim 2, wherein the one or more first coefficients for the positive-pressure non-linear equation are the same as the one or more second coefficients for the negative-pressure non-linear equation.

5. A breathing assistance system according to claim 1, further comprising:

the calibration module being configured to calculate, based on the generated non-linear equation, coefficients for multiple linear equations defining multiple linear line segments corresponding to portions of a curve defined by the non-linear equation; and memory configured to store the calculated coefficients; and the pressure drop calculation module being configured to access the coefficients from the memory for determining pressure drops in gas flowing through the breathing assistance system apparatus for various flow rates.

6. A breathing assistance system according to claim 1, wherein the non-linear equation comprises a second degree polynomial equation.

7. A breathing assistance system according to claim 1, wherein:

the non-linear equation comprises a second degree polynomial equation in the form of:

Pressure Drop=$A$*(Flow Rate)^2+$B$*(Flow Rate); and generating the non-linear equation based at least on the results of the one or more pressure drop calibration tests comprises determining the coefficients A and B for the second degree polynomial equation.

8. A breathing assistance system according to claim 1, wherein the pressure drop calculation module is configured to use the non-linear equation directly to calculate pressure drops in gas flowing through the breathing assistance system apparatus at various flow rates.

9. A breathing assistance system configured to determine pressure drop, comprising:

a gas delivery system configured to deliver gas toward a patient;

one or more sensors configured to measure one or more parameters of gas delivered by the gas delivery system; and a pressure drop compensation system configured to:

perform multiple pressure drop calibration tests, each pressure drop calibration test measuring a pressure drop in gas flowing through a breathing assistance system apparatus at a particular flow rate;

calculate first coefficients for first multiple linear line segments based on the results of first multiple pressure drop calibration tests for a first configuration of the breathing assistance system, the first multiple linear line segments collectively approximating, for the first configuration of the breathing assistance system, a non-linear relationship between (a) pressure drop in gas flowing through the breathing assistance system apparatus and (b) flow rate of gas flowing through the breathing assistance system apparatus;

calculate second coefficients for second multiple linear line segments based on the results of second multiple pressure drop calibration tests for a second configuration of the breathing assistance system, the second multiple linear line segments collectively approximating, for the second configuration of the breathing assistance system, a non-linear relationship between (a) pressure drop in gas flowing through the breathing assistance system apparatus and (b) flow rate of gas flowing through the breathing assistance system apparatus; and store the first calculated coefficients and the second calculated coefficients such that, depending on the current configuration of the breathing assistance system, either the first calculated coefficients or the second calculated coefficients may be accessed while providing breathing assistance to the patient to determine pressure drops in gas flowing through the breathing assistance system apparatus for various flow rates.

10. A breathing assistance system configured to determine pressure drop, comprising:

a gas delivery system configured to deliver gas toward a patient;

one or more sensors configured to measure one or more parameters of gas delivered by the gas delivery system;

memory configured to store:

(a) a first look-up table of coefficients for linear equations representing multiple line segments corresponding to a first configuration of the breathing assistance system, the line segments collectively approximating a non-linear relationship between (a) pressure drop in gas flowing through the breathing assistance system apparatus and (b) flow rate of gas flowing through the breathing assistance system apparatus for the first configuration of the breathing assistance system; and (b) a second look-up table of coefficients for linear equations representing multiple line segments corresponding to a second configuration of the breathing assistance system, the line segments collectively approximating a non-linear relationship between (a) pressure drop in gas flowing through the breathing assistance system apparatus and (b) flow rate of gas flowing through the breathing assistance system apparatus for the second configuration of the breathing assistance system; and a pressure drop compensation system configured to:
receive a measured flow rate value for gas flowing through the breathing assistance system apparatus;
determine whether the breathing assistance system is configured in the first or second configuration;
access from the first or second stored look-up table one or more coefficients corresponding to a particular one of the multiple line segments that corresponds with the measured flow rate value and the determined configuration of the breathing assistance system; and
use the one or more accessed coefficients corresponding to the particular line segment to calculate a pressure drop corresponding with the measured flow rate value.

11. A breathing assistance system configured to determine pressure drop, comprising:
a gas delivery system configured to deliver gas toward a patient;
one or more sensors configured to measure one or more parameters of gas delivered by the gas delivery system;
a calibration module configured to:
perform one or more positive-pressure pressure drop calibration tests, each positive-pressure pressure drop calibration test measuring a pressure drop in gas flowing through a breathing assistance system apparatus at a particular positive flow rate;
perform one or more negative-pressure pressure drop calibration tests, each negative-pressure pressure drop calibration test measuring a pressure drop in gas flowing through a breathing assistance system apparatus at a particular negative flow rate; and
calculate one or more first non-linear equation coefficients corresponding to positive-pressure gas flow based on the results of the one or more positive-pressure pressure drop calibration tests;
calculate one or more second non-linear equation coefficients corresponding to negative-pressure gas flow based on the results of the one or more negative-pressure pressure drop calibration tests; and
generate a non-linear equation relating (a) pressure drop in gas flowing through the breathing assistance system apparatus with (b) flow rate of gas flowing through the breathing assistance system apparatus, the non-linear equation utilizing the one or more first coefficients for a first resulting non-linear curve corresponding to positive-pressure gas flow and the one or more second coefficients for a second resulting non-linear curve corresponding to negative-pressure gas flow; and
a pressure drop calculation module configured to determine pressure drops in gas flowing through the breathing assistance system apparatus for various flow rates based at least on the non-linear equation.

* * * * *